United States Patent
Garcia Perez

(10) Patent No.: US 12,102,304 B2
(45) Date of Patent: Oct. 1, 2024

(54) DEVICE FOR SAMPLING ONE OR MORE ANALYTES

(71) Applicant: GLUCOMODICUM OY, Helsinki (FI)

(72) Inventor: Alejandro Garcia Perez, Helsinki (FI)

(73) Assignee: GLUCOMODICUM OY, Helsinki (FI)

( * ) Notice: Subject to any disclaimer, the term of this patent is extended or adjusted under 35 U.S.C. 154(b) by 585 days.

(21) Appl. No.: 17/440,662

(22) PCT Filed: Feb. 4, 2020

(86) PCT No.: PCT/FI2020/050066
§ 371 (c)(1),
(2) Date: Sep. 17, 2021

(87) PCT Pub. No.: WO2020/188141
PCT Pub. Date: Sep. 24, 2020

(65) Prior Publication Data
US 2022/0151593 A1    May 19, 2022

(30) Foreign Application Priority Data

Mar. 19, 2019 (FI) ..................................... 20195204

(51) Int. Cl.
*A61B 10/00* (2006.01)
*A61B 5/00* (2006.01)
(Continued)

(52) U.S. Cl.
CPC .......... *A61B 10/0045* (2013.01); *A61B 5/002* (2013.01); *A61B 5/14514* (2013.01);
(Continued)

(58) Field of Classification Search
CPC ......... A61B 5/002; A61B 5/05; A61B 5/1451; A61B 5/14514; A61B 5/14532;
(Continued)

(56) References Cited

U.S. PATENT DOCUMENTS

| | | | |
|---|---|---|---|
| 5,964,701 A | * | 10/1999 | Asada .................... A61B 5/002 128/903 |
| 9,711,060 B1 | | 7/2017 | Lusted et al. |

(Continued)

FOREIGN PATENT DOCUMENTS

| | | |
|---|---|---|
| CN | 201767968 | 3/2011 |
| EP | 3 422 936 | 1/2019 |

(Continued)

OTHER PUBLICATIONS

Search Report for FI Application No. 20195204 dated Oct. 14, 2019, 1 page.
International Search Report for PCT/FI2020/050066 dated May 14, 2019, 4 pages.
Written Opinion of the ISA for PCT/FI2020/050066 dated May 14, 2019, 6 pages.

*Primary Examiner* — Eric F Winakur
*Assistant Examiner* — Abel Seifu Abegaz
(74) *Attorney, Agent, or Firm* — NIXON & VANDERHYE

(57) ABSTRACT

Disclosed is a device for non-invasively sampling interstitial fluid including one or more analytes from dermis to the skin surface by employing the magneto-hydrodynamic effect and/or reverse iontophoresis. According to a preferable embodiment the device includes a first frame including a first electrode and a second frame including a second electrode, power source and preferably also a first magnet. The first frame is connected to the second frame by a formable connector adapted to provide mechanical connection between the first frame and the second frame and electrical connection between the power source and the first electrode. The direction of the magnetic field and the direction of the electric current produced by the magnet and the power source is such that the Lorenz force drives the fluid from the dermis towards the skin surface.

18 Claims, 3 Drawing Sheets

(51) Int. Cl.
*A61B 5/145* (2006.01)
*A61B 5/1477* (2006.01)

(52) U.S. Cl.
CPC ........ *A61B 5/14546* (2013.01); *A61B 5/1477* (2013.01); *A61B 5/6832* (2013.01); *A61B 5/746* (2013.01); *A61B 2010/008* (2013.01); *A61B 2560/0425* (2013.01)

(58) Field of Classification Search
CPC .............. A61B 5/14546; A61B 5/1477; A61B 5/150022; A61B 5/150091; A61B 5/150343; A61B 5/6826; A61B 5/6832; A61B 5/746; A61B 10/0045; A61B 2010/008; A61B 2560/0425; A61B 2560/0462

See application file for complete search history.

(56) References Cited

U.S. PATENT DOCUMENTS

| | | |
|---|---|---|
| 2002/0002328 A1 | 1/2002 | Tamada |
| 2002/0193673 A1* | 12/2002 | Fuller ...................... A61B 5/05 600/365 |
| 2018/0070870 A1 | 3/2018 | Emaminejad et al. |

FOREIGN PATENT DOCUMENTS

| | | |
|---|---|---|
| WO | 2010/001122 | 1/2010 |
| WO | 2016/090189 | 6/2016 |
| WO | 2017/019602 | 2/2017 |
| WO | 2017/021585 | 2/2017 |
| WO | 2018/091771 | 5/2018 |

* cited by examiner

DEVICE FOR SAMPLING ONE OR MORE ANALYTES

This application is the U.S. national phase of International Application No. PCT/FI2020/050066 filed Feb. 4, 2020 which designated the U.S. and claims priority to FI Patent Application No. 20195204 filed Mar. 19, 2019, the entire contents of each of which are hereby incorporated by reference.

BACKGROUND OF THE INVENTION

Field of the Invention

This invention relates to devices based on magnetohydrodynamics (MHD) and reverse iontophoresis for sampling fluid, particularly interstitial fluid, comprising one or more analytes.

Description of the Related Art

Interstitial fluid (IF) is an aqueous solution that serves as a transport medium for e.g. glucose and electrolytes between cells and circulatory system. Therefore, the concentration of different solutes such as glucose and lactic acid in IF and in blood exhibits a substantial correlation. This makes the analysis of IF relevant to many developing fields, including medical diagnosis, early disease detection, pharmacokinetics, and smart wearable technologies. Furthermore, a strong commercial and scientific interest promotes research on painless and non-invasive IF sampling methods.

US2002/0002328A1 discloses a noninvasive device and method for sampling IF comprising substances such as glucose through the skin by reverse iontophoresis. The device is designed to monitor blood glucose levels in people with diabetes. The device is not considered a replacement, but an addition to conventional invasive blood glucose monitoring.

WO2010001122A2 discloses a patch for sampling one or more analytes through the skin of a patient. The patch comprises an electrode layer that is positioned adjacent to the skin of a patient and means for actuating an electrode layer to induce the withdrawal of analyte through the skin by reverse iontophoresis. The patch comprises reservoir chambers containing an electrically conducting medium to induce the process of iontophoresis. According to the document, the presence of an electrolyte in liquid form ensures good conductivity between the electrodes and the skin, which enhances the effectiveness of the reverse iontophoresis process. A device 100 suitable for sampling IF from dermis 101a to skin surface by applying magneto-hydrodynamics and reverse iontophoresis is shown in FIG. 1. The device comprises a first electrode 102a and a second electrode 102b adapted to be positioned adjacent to the skin surface 101b, the first electrode separated from the second electrode by a distance 103, a power source 104 adapted to induce an electric current through the first electrode, the interstitial fluid and the second electrode, and also a magnet 105 adapted to produce a magnetic field to the interstitial fluid. Direction of the magnetic field and direction of the electric current produced by the magnet and the power source, respectively, is such that Lorenz force drives the fluid from the dermis 101a towards the skin surface. Furthermore, reverse iontophoresis induced by the electric current contributes to the drag of analytes towards the cathodic i.e. negative electrode 102b. Direction of the current between the first electrode and the second electrode is shown in the figure with a dotted arrow. The electrodes, the magnet and the power source are positioned in a frame 106.

Typically, in devices relying on MHD and reverse iontophoresis, the electrodes adapted to establish electric current through the skin are also adapted to detect or measure one or more analytes. Each electrode can be constituted by a plurality of elements. For instance, each electrode can be constituted by two or more smaller electrodes of different materials forming a galvanic or electrochemical cell. This allows using the electrodes also as sensors to measure or detect glucose, lactic acid and/or other analytes in IF extracted from the dermis. The mechanism for detection or measurement of analytes can rely on enzymatic or non-enzymatic electrochemical reactions.

The precision and accuracy of the measurements based on electrochemical reactions can be easily compromised by poor or unstable electrical or mechanical connection or coupling between the skin and the electrodes including each of their constituting elements. For instance, movement, displacement, or mechanical stress e.g. compression, shear or bending, affecting the sensor and/or the skin in contact with the sensor can lead to erroneous and unreliable measurements. Consequently, MHD and reverse iontophoresis devices are preferable used in anatomical body regions which are less exposed to movement and mechanical stress. Fingers, and particularly, the lateral sides of the proximal and middle phalanges of the fingers offer convenient body regions for the use of MHD or reverse iontophoresis devices because the skin on these regions is less susceptible to mechanical stress caused by the natural movement of the body. Also, the skin on these regions is thin, less hairy, and well irrigated by blood. These features are advantageous for the effectiveness of IF sampling and the accuracy of the measurement.

Unfortunately, miniaturization of devices exploiting MHD and reverse iontophoresis have their challenges. The device must have at least two electrodes adapted to establish an electric current through the electrodes and the skin. Furthermore, the electrodes should be separated from each other to avoid or reduce current leakages through the skin surface. For instance, in the MHD devices the separation between electrodes is typically from 0.5 cm to 5 cm. Also, the sensitivity and detection limit of electrochemical sensors are proportional to their surface area. This imposes restrictions when the concentration of the target analytes is low. Consequently, space requirements limit the implementation of devices based on MHD or reverse iontophoresis in otherwise advantageous body parts. For instance, if the device is in the form of a finger ring, the frame should be sufficiently small, and it should not interfere with the natural movement of the finger.

Thus, there is still a need for further devices for non-invasive sampling of analytes through the skin.

SUMMARY OF THE INVENTION

The present invention is based on the observation that at least some of the state-of-the-art problems related to miniaturization of devices for sampling one or more analytes from IF in non-invasive manner by exploiting the reverse iontophoresis and magneto-hydrodynamic (MHD) phenomenon can be avoided or at least alleviated when the electrodes are positioned in two frames that are electrically and mechanically connected.

Accordingly, it is an object of the present invention to provide a device for sampling dermal interstitial fluid comprising one or more analytes in a non-invasive manner, the device comprising
- a first electrode and a second electrode adapted to be positioned adjacent to the skin surface,
- a power source adapted to induce an electric current through the first electrode, interstitial fluid and the second electrode,
- a first frame adapted to position the first electrode,
- a second frame adapted to position the second electrode and the power source, and
- a formable connecting means adapted to provide mechanical connection between the first frame and the second frame and electric connection between the power source and the first electrode, and wherein the electric current is adapted to produce reverse iontophoresis to drive the interstitial fluid from dermis towards the skin surface.

Further objects of the present invention are described in the accompanying dependent claims.

Exemplifying and non-limiting embodiments of the invention, both as to constructions and to methods of operation, together with additional objects and advantages thereof, are best understood from the following description of specific exemplifying embodiments when read in connection with the accompanying drawings.

The verbs "to comprise" and "to include" are used in this document as open limitations that neither exclude nor require the existence of un-recited features. The features recited in the accompanied depending claims are mutually freely combinable unless otherwise explicitly stated. Furthermore, it is to be understood that the use of "a" or "an", i.e. a singular form, throughout this document does not exclude a plurality.

DESCRIPTION OF THE PREFERRED EMBODIMENTS

Figure 1:
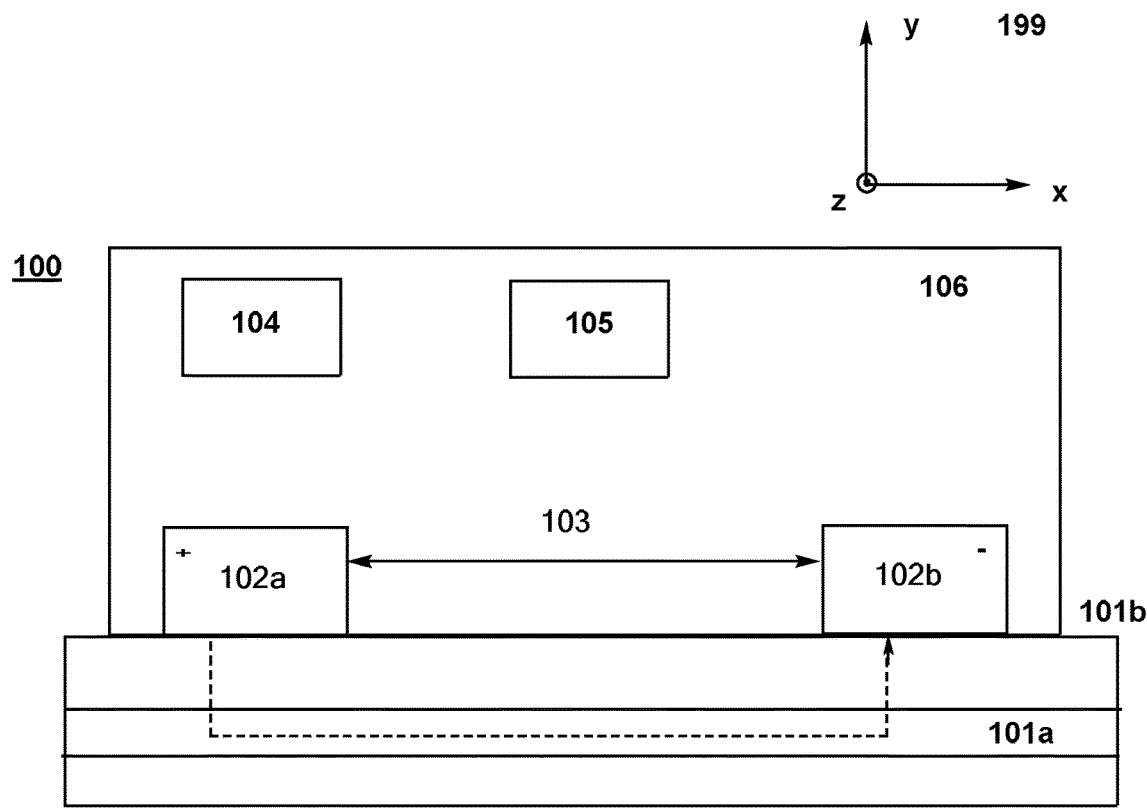
FIG. 1 shows a prior art device for sampling an analyte such as glucose from dermis using reverse iontophoresis and magnetohydrodynamic phenomenon.

FIG. 1 has been discussed in the Background section of this document.

The present invention concerns a device, such as a ring for sampling IF in a non-invasive manner, wherein the IF comprises one or more analytes to be investigated. According to the invention, IF is sampled from the dermis by exploiting reverse iontophoresis and preferably also the MHD phenomenon.

Devices according to exemplifying and non-limiting embodiments of the invention are shown in FIGS. 2-5. In the exemplary figures, the first electrode serves as an anode, and the second electrode is serves as a cathode.

Figure 2:
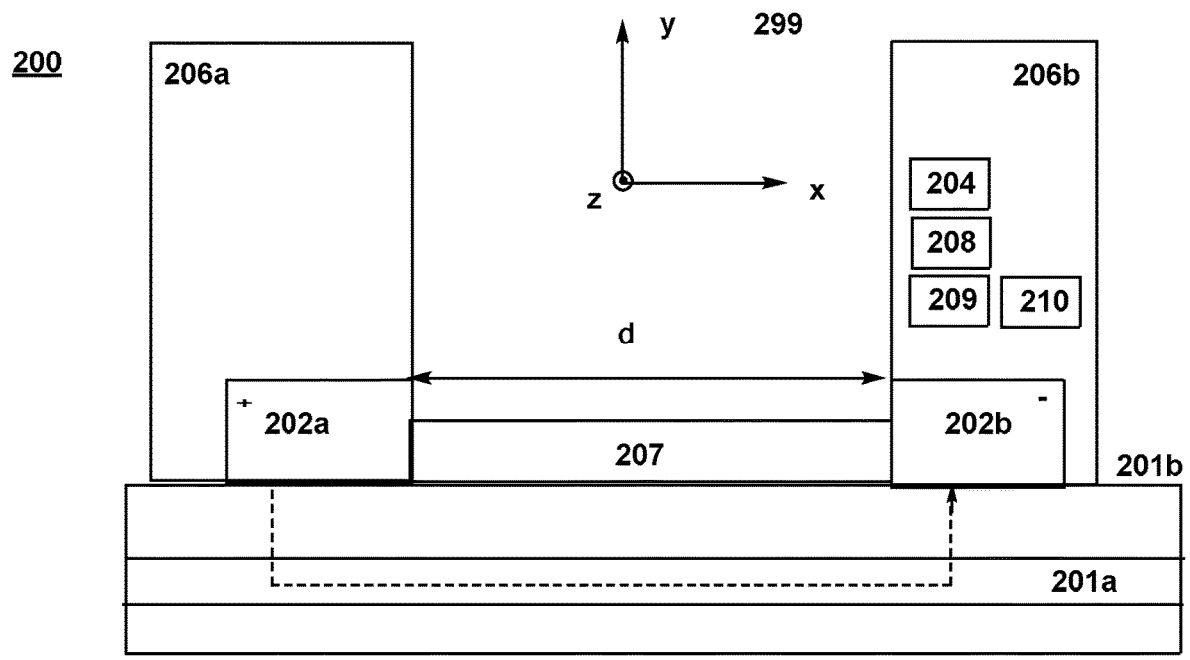
FIG. 2 illustrates a device according to an exemplifying and non-limiting embodiment of the invention using reverse iontophoresis.

A device 200 according to one embodiment of the present invention is shown in FIG. 2. The device comprises
- a first frame 206*a* comprising a first electrode 202*a*,
- a second frame 206*b* comprising
  - a second electrode 202*b*, and
  - a power source 204 adapted to induce an electric current through the first electrode, interstitial fluid and the second electrode, and
- a formable connecting means 207 adapted to provide mechanical connection between the first frame and the second frame and electric connection between the power source and the first electrode.

The first electrode and a second electrode are adapted to be positioned adjacent to the skin surface 201*b*. The direction of the current between the first electrode and the second electrode is shown in the figure with a dotted arrow. Reverse iontophoresis produced by the electric current is adapted to drive the IF from dermis 201*a* towards the skin surface at the second electrode.

According to this embodiment, reverse iontophoresis promotes movement of the IF towards the second electrode-skin interface and thus sampling of the IF takes place only at the second frame. The first electrode serves only to establish the electric current.

Figure 3:
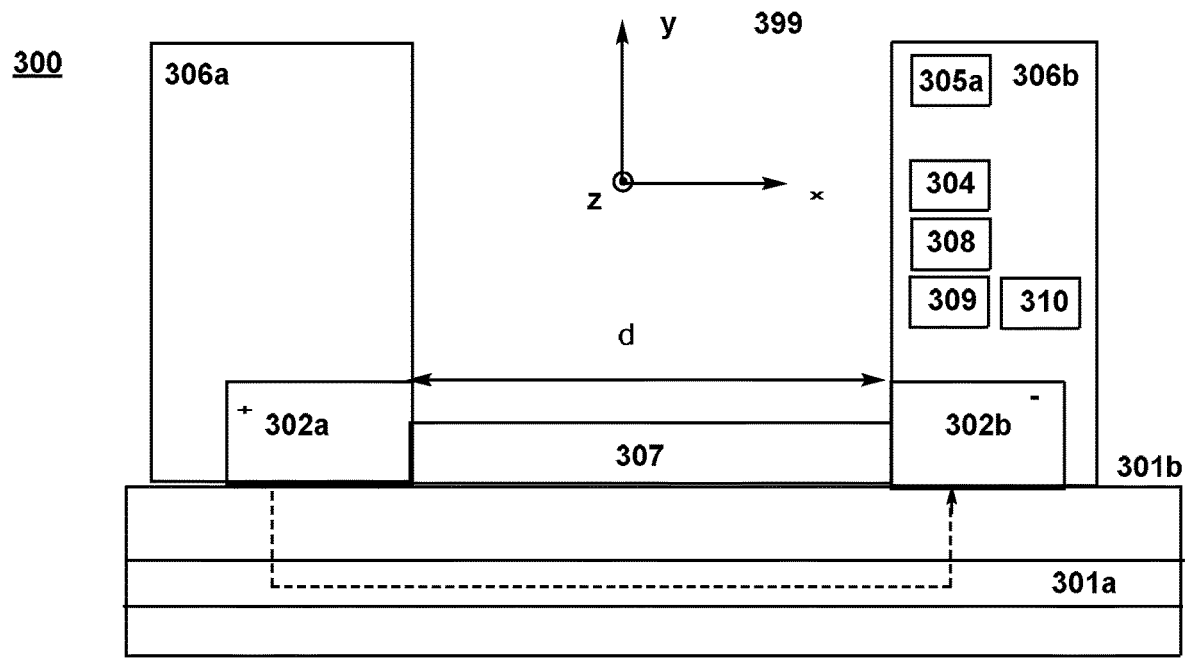
FIGS. 3 and 4 illustrate devices according to exemplifying and non-limiting embodiments of the invention using reverse iontophoresis and magnetohydrodynamic phenomenon.

According to another embodiment of the present invention, IF is sampled from the dermis by the MHD phenomenon and reverse iontophoresis. This is preferable since the MHD phenomenon allows more efficient sampling of the IF than reverse iontophoresis alone. A device 300 according to one preferable embodiment of the present invention is shown in FIG. 3. The device comprises
- a first frame 306*a* comprising a first electrode 302*a*
- a second frame 306*b* comprising
  - a second electrode 302*b*,
  - a power source 304 adapted to induce an electric current through the first electrode, the interstitial fluid and the second electrode, and
  - a first magnet 305*a* adapted to induce magnetic field to the interstitial fluid, and
- a formable connecting means 307 adapted to provide mechanical connection between the first frame and the second frame and electric connection between the power source and the first electrode.

The first electrode and the second electrode are adapted to be positioned adjacent to the skin surface 301*b*. The direction of the magnetic field produced by the first magnet and the direction of the electric current produced by the power source is adapted to be such that the Lorentz force drives the interstitial fluid from the dermis 301*a* substantially towards the skin surface. Furthermore, the reverse iontophoresis produced by the electric current is adapted to drive the IF towards the second electrode. The direction of the current between the first electrode and the second electrode are shown in the figure with a dotted arrow.

Figure 4:
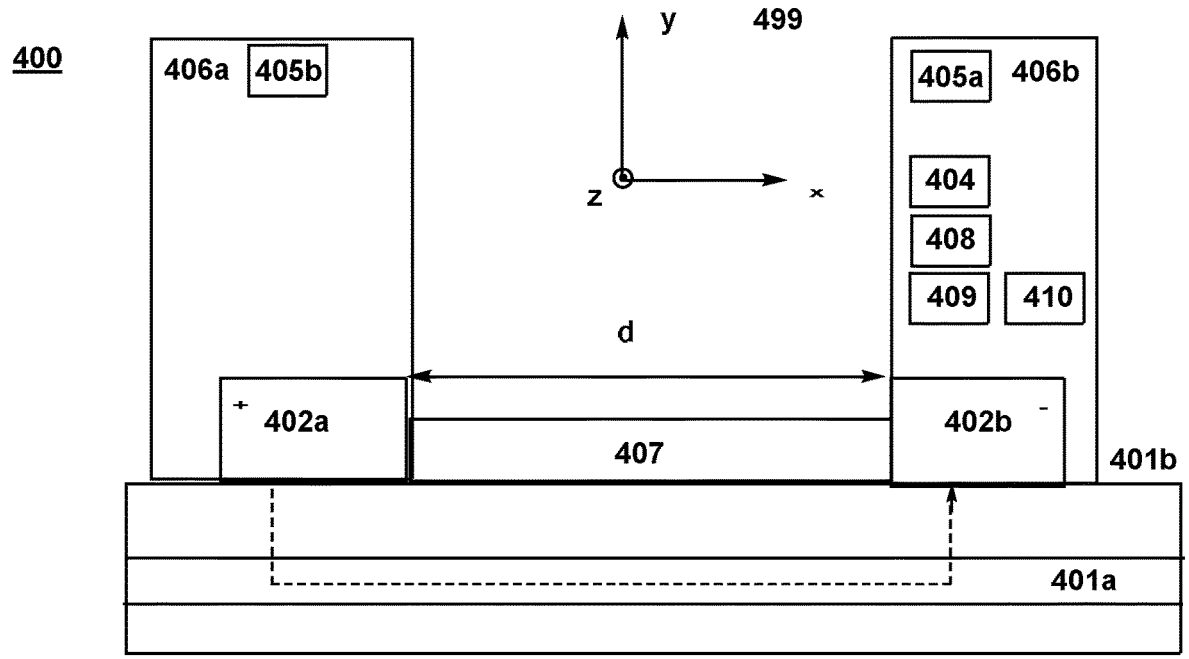

A device 400 according to another preferable embodiment of the present invention exploiting the MHD phenomenon and reverse iontophoresis is shown in FIG. 4. The device comprises
- a first frame 406*a* comprising
  - a first electrode 402*a* and
  - a second magnet 405*b*,
- a second frame 406*b* comprising
  - a second electrode 402*b*,
  - a first magnet 405*b*, and a power source 404 adapted to induce an electric current through the first electrode, the interstitial fluid and the second electrode, and a formable connecting means 407 adapted to provide mechanical connection between the first frame and the second frame and electric connection between the power source and the first electrode.

The first electrode and a second electrode are adapted to be positioned adjacent to the skin surface 401*b*, and the first magnet and the second magnet are adapted to induce a magnetic field in the interstitial fluid. The direction of the magnetic field produced by the magnets and the direction of the electric current produced by the power source is adapted to be such that the Lorentz force drives the interstitial fluid from the dermis 401*a* substantially towards the skin surface. Furthermore, reverse iontophoresis induced by the electric current is adapted to drive the IF towards the first electrode or the second electrode. When reverse iontophoresis is adapted to drive IF towards the second electrode, the direction of the current between the first electrode and the second electrode is as shown in FIG. 4 with a dotted arrow. The opposite direction can be used to drive IF towards the first electrode.

The embodiment described in FIG. 4 enables sampling of interstitial fluid in both the first frame and in the second frame.

Reverse iontophoresis induced by the electric current contributes to the drag of analytes towards the cathodic i.e. negative electrode. Therefore, using the first electrode as cathode and the second electrode as anode increases the sampling rate within the first frame. Consistently, using the second electrode as cathode and the first electrode as anode increases the sampling rate towards the second frame. When the first electrode works as cathode, the magnetic field of the second magnet should be oriented so that dermal interstitial fluid is driven by the Lorentz force towards the skin surface near the first frame. When the second electrode works as cathode, the magnetic field of the first magnet should be oriented so that dermal interstitial fluid is acted by Lorentz force towards the skin surface near the second frame. This can be implemented by positioning the first magnet and the second magnet in such a way that their magnetic fields point in opposite directions.

The current density near the electrodes is substantially higher as compared to further from the electrodes. This results in a stronger Lorentz force acting on the interstitial fluid and in a higher extraction rate near the electrodes i.e. in proximity of the first frame and of the second frame.

According to a preferable embodiment the first frame and/or the second frame comprises means 208, 308, 408 adapted to collect and/or store the one or more analytes sampled from the dermis.

Figure 5:
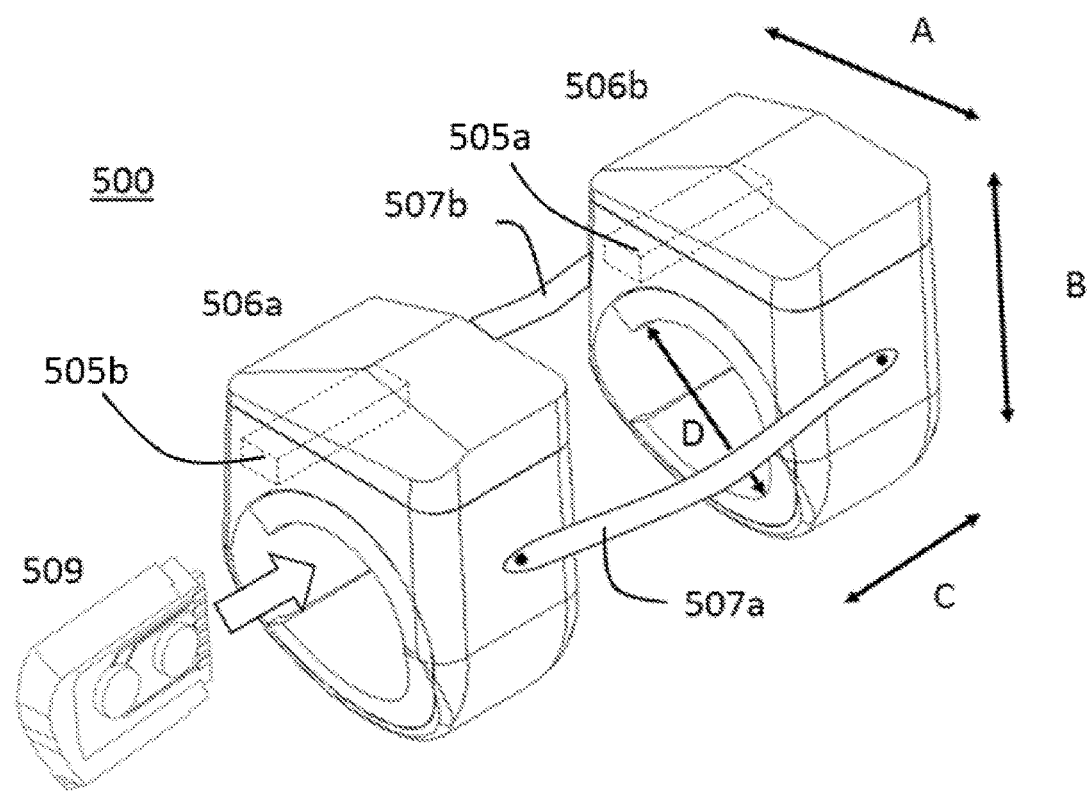
FIG. 5 illustrates a schematic view of a device in form of a finger ring comprising a disposable sensor according to an exemplifying and non-limiting embodiment of the invention.

According to another preferable embodiment, the first frame and/or the second frame comprises means such as a sensor 209, 309, 409, 509 adapted to analyze the one or more analytes. According to an exemplary embodiment, the first and/or the second frame includes an electrochemical sensor, such as a screen-printed biosensor, to measure analytes such as glucose in the sampled interstitial fluid. The sensor can be part of a disposable element that is replaced after a certain period. An exemplary device 500 comprising a disposable sensor 509 adapted to be attached to the first frame 506*a* is shown in FIG. 5.

According to a preferable embodiment the sensor is incorporated to the first electrode and/or the second electrode. Thus, the electrodes adapted to establish electric current through the skin are also adapted to detect or measure one or more analytes. Each electrode can be constituted by a plurality of elements. For instance, each electrode can be constituted by two or more smaller electrodes of different materials forming a galvanic or electrochemical cell. This allows using the electrodes also as sensors to measure or detect glucose, lactic acid and/or other analytes in IF extracted from the dermis. The mechanism for detection or measurement of analytes can rely on enzymatic or non-enzymatic electrochemical reactions.

The higher extraction rate of interstitial fluid facilitates the measurement of analytes. The sensor or sensors can be chosen based on the target analyte or analytes. Exemplary but not limiting sensors include optical sensors and electrochemical sensors or biosensors relying on enzymatic or non-enzymatic reactions.

The device of the present invention includes a formable connecting means. As defined herein the term formable connecting means should be understood as an element or array of elements which are flexible and/or curved in compression but linear, rigid, and load-bearing in tension. The formable connecting means allows flexing the finger when the device is positioned around a finger such that the first frame is at one side of a joint and the second frame is at another side of the joint i.e. proximal and middle phalanges. The formable connecting means should not restrict the movement of the finger. An exemplary device 500 wherein the first frame 506*a* is connected to the second frame 506*b* by a pair of formable connecting means 507*a,b* is shown in FIG. 5. Shapes and dimensions of the first frame and the second frame can be chosen as desired. Exemplary dimension or a frame of a device adapted to be positioned around a finger are shown in the figure. The dimensions in direction A, B, C, and D are typically 3-15 mm, 5-30 mm, 5-50 mm, and 6-30 mm, respectively. In the figure, positioning of the first magnet 505*a* and the second magnet 505*b* are also shown.

The formable connecting means includes typically at least one string, wire, or cable of electrically conducting material which is preferably insulated. Suitable insulating materials include but are not limited to chlorinated polyethylene (CPE), ethylene propylene diene monomer (EPDM), ethylene tetrafluroroethylene (ETFE), fluorinated ethylene (FEP), foamed FEP, foamed PFA, foamed PE, foamed TPE, high density polyethylene (HDPE), low density polyethylene (LDPE), modified polyphenylene (mPPE), neoprene, polyethylene (PE), perfluoroalkoxy (PFA), perfluoroelastomer (PFE), polypropylene (PP), polytetrafluoroethylene (PTFE), polyurethane (PUR), polyvinyl Chloride (PVC), silicone, tetrafluoroethylene (TFE), thermoplastic elastomer (TPE), thermoplastic rubber (TPR), cross-linked polyethylene (XLPE), cross-linked polyolefin (XLPO).

According to one embodiment the one or more cables encompass one or more solid wires of conducting or semiconducting material or combination of materials. In another embodiment the one or more cables encompass two or more wires of conducting or semiconducting material which are braided or stranded to increase the flexibility of the cable.

The length of the formable connecting means is typically 1 mm-5 cm, preferably 5 mm-3 cm, which is also preferably the distance d between the first electrode and the second electrode when the device is in x-direction of the coordinate systems 299, 399 and 499.

According to one embodiment, the wires or cables are accompanied by jewelry elements such as metal chains. Exemplary metals are gold, silver and platinum. According to another embodiment, the wires or cables are integrated into decoration elements. The decorating elements may be made of wood, plastic, metal, or flexible materials.

According to one embodiment, the first and/or the second frame include electronic circuits, batteries, connectors, displays, light indicators, sound indicators, and/or antennas. The electronic circuits 210, 310, 410 enable, for instance, driving the sensors such as establishing a bias voltage to the sensor to trigger a sensor response, processing the signal from the sensor including analog signal processing and conditioning, acquiring a signal from the sensor such as performing analog to digital conversion, applying mathematical algorithms including artificial intelligence and digital signal processing, displaying data, sending data, receiving data or commands, activating alarms, implementing a user interface, or transmitting data via Bluetooth or Wi-Fi.

According to one embodiment, the first frame can be disconnected from and reconnected to the second frame and the formable connecting means. This allows the user to remove one frame e.g. one piece of the ring while the device is not in use.

According to one embodiment, the first frame and/or the second frame comprises actuating mechanisms, such as electromechanical, electro-pneumatic, or chemodynamical mechanisms to physically enhance the electrical and mechanical connection between the electrode or electrodes and the skin temporarily e.g. while performing a measurement.

According to one embodiment, the first frame and/or the second frame comprises means to measure the temperature and to control the temperature at a certain space in the frame, for instance close electrochemical sensors which are sensitive to temperature.

According to an exemplary embodiment the surface of the first electrode and the surface of the second electrode contain silver-silver chloride (Ag—AgCl), carbon, and/or an inert and non-ferromagnetic material. Exemplary further materials are carbon, gold, platinum and polymers such as lithium polymer.

The electrodes can be coated with different materials. Also, the electrodes can feature a sensor or matrix of sensors involving multiple materials including enzymes and catalysts such as glucose oxidase, dehydrogenase and Prussian blue. Furthermore, different materials or combination of materials can be used as an interface between the electrodes and the skin for instance to optimize the sensor at the same time for both low and high ranges of glucose concentration, reduce the electric impedance, to protect the electrode coating i.e. enzymes and to facilitate the analysis of the extracted IF samples. The electrode skin interface can serve to induce or promote the occurrence of desirable concentration gradients of, for instance, the target analyte, the agents that reacts with the target analyte, the agents reacting at the electrode surface, or the products of the different reactions. Suitable materials for this purpose include biocompatible gel, hydrogels, and permeable and semipermeable membranes made of e.g. regenerated cellulose, silicone and monofilament fabric of polyamide.

The interface serves to maintain a low electric impedance between the electrodes and the skin, to facilitate the transport of analytes towards the device, to preserve electrochemical conditions such as pH and activity of the enzyme. In one embodiment, the electrode skin interface is preferably a gel or a hydrogel. In another preferred embodiment, the electrode skin interface is a membrane which is permeable or semipermeable, electrically conductive, and hypoallergenic. Exemplary materials suitable for this purpose include biocompatible permeable and semipermeable membranes made of regenerated cellulose, silicone and monofilament fabric of polyamide. These membranes can be treated with agents that work as humectants to help maintain the desired pose structure and to increase its electric conductivity. Exemplary agents are glycerol, agarose gel, and phosphate buffered saline.

The membranes can also be loaded with agents, such as corticosteroids and other drugs, to prevent or reduce potential skin reactions induced by the extraction procedure.

Furthermore, the interface can be loaded with enzymes and catalysts. The interface can also comprise an electrically conductive or insolating and permeable or impermeable mask to tailor the electric field or to guide the extracted fluid towards a sensor.

According to the exemplary embodiments shown in FIGS. 2-4, the first electrode acts as a positive (anodic) electrode and the second electrode acts as a negative (cathodic) electrode. The polarity of the electrodes can be flipped, and other configurations are possible. The first electrode and the second electrode are preferably substantially parallel to each other. The device may include a plurality of first electrodes and a plurality of second electrodes. The electrodes can be identical of different.

The first electrode and the second electrode comprise a contact surface. According to one exemplary embodiment, the contact surface of the electrodes is flat and either circular e.g. disk-shaped, rectangular, elliptical or pyramidal. According to another embodiment the contact surface is adapted to the shape of the skin surface. For example, if the skin is on a finger, the contact surface may be curved to allow maximal mechanical and electric contact with the skin. The contact surface may comprise extrusions and/or protrusions to facilitate maximal adherence to the skin surface.

The area of the contact surface of each electrode is preferably between 0.01 $cm^2$ and 9 $cm^2$, and most preferably between 0.15 $cm^2$ and 1 $cm^2$. The distance d between the first electrode and the second electrode is preferably between 1 mm and 5 cm, and most preferably between 5 mm and 3 cm. According to an exemplary embodiment the distance is 1 cm.

According to one embodiment, the shape of the contact surface of the electrodes is elliptical, and the major axis of the ellipsis is substantially longer than the minor axis. This allows to set a larger current density through the dermis without increasing the current density at the electrode-skin interface. The current density through the target such as skin can be different in all cases even if the contact area of the electrodes is the same. The electrode shape can alter the distribution of electric current in the skin, and therefore, the local current density to increase the Lorentz force and the extraction rate of IF. For this reason, the elliptical electrode shapes illustrated in case are preferable.

According to one embodiment the first electrode and/or the second electrode is adapted to be installed in and disposed from the first frame and/or the second frame.

The power source can be a direct current (DC) power source and/or an alternating current (AC) power source that limits and regulates the energy i.e. the intensity of the electric current and/or voltage delivered through the electrodes. According to an exemplary embodiment, the power source is a floating current source that provides means to establish a direct electric current preferably in the range of 10 µA to 10 mA, and more preferably in the range 0.1 mA to 1 mA. The current density at the electrode-target, such as skin interface is preferably between 1 $\mu A/cm^2$ and 10 $mA/cm^2$, and most preferably between 0.1 $mA/cm^2$ and 1 mA/cm². The voltage provided by the current source is preferable between 1 V and 100 V. The power source can be positioned at the first frame and/or the second frame.

In a particular embodiment, the electric current established by the floating current source exhibits a unipolar, i.e. unidirectional or bipolar such as bidirectional waveform or alternating waveform. The frequency of the electric signal is preferably between 0.1 Hz and 100 kHz, and more preferably between 10 Hz and 10 kHz. The electric signal can be modulated in amplitude and/or frequency, and can have different waveforms, for instance, sine, square, pulsed such as rectangular, triangle, and saw tooth. Also, the signal can be burst- and/or duty-cycle-modulated.

According to one embodiment the power source comprises a disposable or rechargeable battery and/or a wearable energy harvesting means. For instance, the energy can be generated from the movement of human joints by applying existing technologies or technologies developed in the future.

The magnet can be a permanent magnet or an electromagnet. The intensity of the magnetic field at the surface of the magnet is preferably between 0.01 mT and 2 T, and most preferably between 0.1 mT and 500 mT. The distance between the magnet and the electrodes is preferably less than 1 cm. According to an exemplary embodiment, the magnetic field is provided by a neodymium magnet located 0.5 cm apart from the skin surface when the device is at its operational position. Also, when the device is at its operational position, the direction of the magnetic field is substantially perpendicular to the skin surface and substantially perpendicular to desired direction of fluid displacement from the dermis to the skin surface. Consequently, the dermal IF is driven towards the surface of the skin.

According to another embodiment the device comprises a plurality of magnets. According to an exemplary embodiment, the magnetic field is provided by an array of magnets or electromagnets. An exemplary array is a Halbach array.

The use of arrays of magnets allows to modulate the magnetic field directionally or locally: e.g. to augment, decrease or cancel the field. For instance, a circular Halbach array consisting on a cylinder composed of neodymium magnets can be used to produce an intense magnetic field confined within the cylinder. Moreover, the array of magnets can be wrapped around the electrode and the extraction site, for instance in a ring, where the electrodes are arranged inside the cylinder. This allows having a strong magnetic field at the extraction site while keeping a week magnetic field elsewhere.

Further embodiments are disclosed in the following numbered clauses.

1. A method for sampling dermal interstitial fluid comprising one or more analytes, the method comprising steps of:
    a) providing a device comprising
        a first electrode and a second electrode adapted to be positioned adjacent to the skin surface,
        a power source adapted to induce an electric current through the first electrode, interstitial fluid and the second electrode,
        a first magnet adapted to induce a magnetic field to the interstitial fluid wherein direction of the magnetic field produced by the magnet and direction of the electric current produced by the power source is adapted to be such that Lorentz force drives the interstitial fluid from the dermis substantially towards the skin surface wherein the device comprises
        a first frame adapted to position the first electrode,
        a second frame adapted to position the second electrode, the power source and the first magnet and
        a formable connecting means adapted to provide mechanical connection between the first frame and the second frame and electric connection between the power source and the first electrode,
    b) positioning the first electrode and a second electrode adjacent to the skin surface,
    c) inducing an electric current through the first electrode, the interstitial fluid and the second electrode, and
    d) inducing a magnetic field to the interstitial fluid comprising one or more analytes, wherein the direction of the magnetic field and the electric current is such that Lorentz force drives the interstitial fluid from the dermis towards the skin surface.

2. The method according to clause 1 comprising a step of
    e) collecting the interstitial fluid.

3. The method according to clause 2 comprising a step of
    f) analyzing the one or more analytes.

4. The method according to any or clauses 1-3, wherein the one or more analytes comprises one or more of amino acids, sugars, fatty acids, co-enzymes, hormones, neurotransmitters, lactic acid, drugs.

5. The method according to any of clauses 1-4 wherein the analyte is glucose, potassium, dopamine, ethanol, sodium, cortisol, melatonin, vitamin C, testosterone, proteins, drugs, and/or lactic acid.

6. The method according to any of clauses 1-5 wherein the analyte is glucose.

7. A method for sampling dermal interstitial fluid comprising one or more analytes, the method comprising steps of:
    a) providing a device comprising
        a first electrode and a second electrode adapted to be positioned adjacent to the skin surface,
        a power source adapted to induce an electric current through the first electrode, interstitial fluid and the second electrode,
        a first frame adapted to position the first electrode,
        a second frame adapted to position the second electrode and the power source and
        a formable connecting means adapted to provide mechanical connection between the first frame and the second frame and electric connection between the power source and the first electrode,
    b) positioning the first electrode and a second electrode adjacent to the skin surface,
    c) inducing an electric current through the first electrode, the interstitial fluid and the second electrode, such that reverse iontophoresis produced by the electric current drives the interstitial fluid from dermis towards the skin surface.

8. The method according to clause 7 comprising a step of
    e) collecting the interstitial fluid.

9. The method according to clause 8 comprising a step of
    f) analyzing the one or more analytes.

10. The method according to any or clauses 7-9, wherein the one or more analytes comprises one or more of amino acids, sugars, fatty acids, co-enzymes, hormones, neurotransmitters, lactic acid, drugs.

11. The method according to any of clauses 7-10 wherein the analyte is glucose, potassium, dopamine, ethanol, sodium, cortisol, melatonin, vitamin C, testosterone, proteins, drugs, and/or lactic acid.

12. The method according to any of clauses 7-11 wherein the analyte is glucose.

The specific examples provided in the description given above should not be construed as limiting the scope and/or the applicability of the appended claims.

What is claimed is:

1. A device for sampling dermal interstitial fluid comprising one or more analytes, the device comprising
   a first electrode and a second electrode adapted to be positioned adjacent to a skin surface,
   a power source adapted to induce an electric current through the first electrode, interstitial fluid and the second electrode, and
   a first frame adapted to position the first electrode, wherein the electric current is adapted to produce reverse iontophoresis to drive the interstitial fluid from dermis towards the skin surface, wherein the device comprises
   a second frame adapted to position the second electrode and the power source, and
   a formable connecting means adapted to provide mechanical connection between the first frame and the second frame and electric connection between the power source and the first electrode, and wherein the second frame comprises a first magnet adapted to induce a magnetic field in the interstitial fluid, and wherein direction of the magnetic field produced by the first magnet and direction of the electric current is adapted to be such that Lorentz force drives the interstitial fluid from the dermis towards the skin surface,
   the first frame comprises a second magnet adapted to induce a magnetic field in the interstitial fluid, and wherein direction of the magnetic field produced by the second magnet and the direction of the electric current is adapted to be such that Lorentz force drives the interstitial fluid from the dermis towards the skin surface, and wherein the polarity of the first magnet is opposite to the polarity of the second magnet.

2. The device according to claim 1, wherein direction of the electric current produced by the power source is alternating.

3. The device according to claim 2, wherein the direction of the magnetic field produced by the first magnet is adapted to be such that Lorentz force drives the interstitial fluid from the dermis towards the skin surface when the second electrode serves as cathode.

4. The device according to claim 2, wherein the direction of the magnetic field produced by the second magnet is adapted to be such that Lorentz force drives the interstitial fluid from the dermis towards the skin surface when the first electrode serves as cathode.

5. The device according to claim 1, wherein surface of the first electrode and the surface of the second electrode are adapted to be substantially parallel to the skin surface when the device is at its operational position.

6. The device according to claim 1, wherein length of the formable connecting means is 1 mm-5 cm.

7. The device according to claim 1, wherein the formable connecting means comprises at least one wire or cable made of electrically conductive material, and wherein the at least one wire or cable is coated with an insulating material.

8. The device according to claim 1, wherein the first frame and/or the second frame comprises means adapted to collect and/or store one or more analytes sampled from the dermis.

9. The device according to claim 1, wherein the first frame and/or the second frame comprises a sensor adapted to analyze, detect and/or measure concentration of the one or more analytes.

10. The device according to claim 9, wherein the sensor is part of the first electrode and/or the second electrode.

11. The device according to claim 9, wherein the first frame and/or the second frame comprises electronic circuits adapted to one or more of: drive the sensors, process a signal from the sensor, acquire a signal from the sensor, apply mathematical algorithms, display data, send data, receive data or commands, activate alarms, implement a user interface, and transmit data via Bluetooth or Wi-Fi.

12. The device according to claim 1, wherein the first electrode and/or the second electrode is adapted to be installed in and disposed from the first frame and/or the second frame.

13. The device according to claim 1, wherein the first electrode and/or the second electrode comprises adhesive material adapted to be positioned in contact with the skin surface.

14. The device according to claim 1, wherein the first frame is adapted to be disconnected from and connected to the second frame and the formable connecting means.

15. The device according to claim 1, wherein the power source comprises disposable or rechargeable battery.

16. The device according to claim 1, wherein the power source comprises a wearable energy harvesting means.

17. The device according to claim 1, wherein the first frame and/or the second frame comprises means adapted to measure temperature and to control the temperature of a part of the first frame and/or the second frame.

18. The device according to claim 1, wherein length of the formable connecting means is 5 mm-3 cm.

* * * * *